United States Patent [19]

Frame

[11] 3,978,137

[45] Aug. 31, 1976

[54] OXIDATION OF SULFUR-CONTAINING COMPOUNDS

[75] Inventor: Robert R. Frame, Glenview, Ill.

[73] Assignee: Universal Oil Products Company, Des Plaines, Ill.

[22] Filed: Mar. 14, 1975

[21] Appl. No.: 558,407

[52] U.S. Cl............................. 260/608; 208/207; 423/573 R
[51] Int. Cl.².................................. C07C 148/06
[58] Field of Search.................. 260/608; 208/207; 423/573

[56] References Cited
UNITED STATES PATENTS

| | | | |
|---|---|---|---|
| 2,921,020 | 1/1960 | Urban et al. | 260/608 |
| 2,921,021 | 1/1960 | Urban et al. | 260/608 |
| 3,230,180 | 1/1966 | Larson et al. | 208/207 |
| 3,565,959 | 2/1971 | Takase et al. | 260/608 |
| 3,709,983 | 1/1973 | Hamblin | 423/573 |

*Primary Examiner*—Lewis Gotts
*Assistant Examiner*—D. R. Phillips
*Attorney, Agent, or Firm*—James R. Hoatson, Jr.; Raymond H. Nelson; William H. Page, II

[57] ABSTRACT

A process is disclosed which comprises the oxidation of sulfur-containing compounds by treating said sulfur-containing compounds with an oxygen-containing gas in a medium possessing a $pH$ in a range of from about a $pH$ of 8 to a $pH$ of about 14 in the presence of a catalyst system comprising a Group VIIB metal phthalocyanine and a Group VIII metal phthalocyanine.

23 Claims, No Drawings

OXIDATION OF SULFUR-CONTAINING COMPOUNDS

This invention relates to a process for the oxidation of sulfur-containing compounds. More specifically, this invention relates to the oxidation of sulfur-containing compounds which comprises the treatment of said sulfur-containing compounds with an oxygen-containing gas in a medium possessing a $pH$ in a range of from about a $pH$ of 8 to a $pH$ of about 14 in the presence of a catalyst system comprising a Group VIIB metal phthalocyanine and a Group VIII metal phthalocyanine.

The oxidation of various sulfur-containing compounds is well-known in the prior art. The oxidation reactions known in the art are mainly directed to the oxidation of mercaptans to disulfides and the oxidation of hydrogen sulfide to sulfur. Various modes of operation have been set forth, however, most generally the oxidation reactions have been performed catalytically in an alkaline environment. It has been shown that various catalysts have been utilized in the oxidation reactions, the most notable consisting of different metal chelates such as metal phthalocyanines. The metal phthalocyanine catalysts have been shown to include cobalt phthalocyanine, vanadium phthalocyanine, iron phthalocyanine, copper phthalocyanine, nickel phthalocyanine, molybdenum phthalocyanine, chromium phthalocyanine, tungsten phthalocyanine, magnesium phthalocyanine, platinum phthalocyanine, hafnium phthalocyanine, palladium phthalocyanine, etc. Further, the catalysts of the prior art have been shown to be used in an aqueous liquid-liquid form or in a solid form dispersed on a solid support.

In contradistinction to the prior art, it has now been discovered that a catalyst system comprising a Group VIIB phthalocyanine and a Group VIII phthalocyanine can be utilized in the oxidation of sulfur-containing compounds. Many sulfur-containing compounds, especially mercaptans and hydrogen sulfide, which are formed in many industrial processes or occur naturally in crude oil, must be converted to other compounds before disposal as a result of environmental considerations. For example, hydrogen sulfide has a high oxygen demand and accordingly will deprive marine life and other living organisms of oxygen needed for survival. Also, most mercaptan compounds possess a pungent odor which is harmful and displeasing to the surrounding environment.

Previous metal phthalocyanine catalyst systems set forth in the prior art possess problems of hydrogen peroxide production which causes overoxidation of the sulfur-containing compounds. The overoxidation of the sulfur-containing compounds presents problems of color generation, which is highly undesirable in the treatment of petroleum charge stocks, and of consumption of caustic or ammonia, which is normally utilized in the oxidation of both mercaptans and hydrogen sulfide. The utilization of the present catalyst system will greatly reduce the production of hydrogen peroxide, and therefore overoxidation of the entire system. The lack of overoxidation will alleviate the presence of any side oxidation products which would create consumption of caustic and color formation within the recovered charge stock. The utilization of the present invention will also allow the refiner or manufacturer a catalytic treating method which is more economically feasible as a result of the eradication of any necessary subsequent treatment steps to remove color-generating compounds and the extended "use time" for the caustic medium of the various treatment processes. The above catalyst system will also create new combinations of metal phthalocyanine catalytic compositions of matter as a result of the two component system, therefore, different impregnation and dispersal effects can further be studied to maximize catalytic treatment conditions.

The utility of the present invention resides in the environmental necessity to treat potentially ecologically harmful compounds such as mercaptans and hydrogen sulfide. Likewise, the products formed from the oxidation of these potentially ecologically dangerous species possess utility of their own. For example, sulfur is the resultant oxidation product from the oxidation of hydrogen sulfide, said sulfur is utilized in the chemical industry in the production of sulfuric acid; in pulp and paper manufacturing; as an agricultural fungicide; in rubber vulcanization; in the preparation of various medicines; etc. Likewise, various disulfides which are separated and recovered subsequent to the oxidation of mercaptan compound can be selectively reduced back to mercaptan compounds for selective use in natural gas for safety purposes.

Therefore, one object of our invention is to provide a process for the oxidation of sulfur-containing compounds.

Further, it is an object of our invention to provide a process for the oxidation of sulfur-containing compounds utilizing a novel catalytic composition of matter.

In one aspect an embodiment of this resides in a process for the oxidation of sulfur-containing compounds which comprises the treatment of said sulfur-containing compounds with an oxygen-containing gas in a medium possessing a pH in a range of from about a $pH$ of 8 to a $pH$ of 14 in the presence of a catalyst system comprising a Group VIIB metal phthalocyanine and a Group VIII metal phthalocyanine at oxidation conditions, and recovering the resultant oxidized sulfur-containing compound.

A specific embodiment of the present invention resides in a process for the treatment of a petroleum charge stock containing mercaptan compounds with oxygen in the presence of a catalyst comprising 3 parts manganese phthalocyanine and 1 part cobalt phthalocyanine in a medium comprising sodium hydroxide ($pH$ of 12) at a temperature of from about 100° C. to about 500° C. and a pressure of about 1 atmosphere to about 100 atmospheres and recovering the resultant oxidized petroleum charge stock.

Another specific embodiment resides in a process for the treatment of an aqueous stream containing hydrogen sulfide with oxygen in the presence of a catalyst comprising 3 parts manganese phthalocyanine and 1 part cobalt phthalocyanine in a medium comprising ammonia ($pH$ of 10 ) at a temperature of 52° C. and a pressure of 5 atmospheres and recovering the resultant oxidized aqueous stream.

Other objects and embodiments are set forth in the following further description of the present invention.

As hereinbefore set forth, the present invention is concerned with the treatment of a stream containing a sulfur-containing compound with an oxygen-containing gas in a medium possessing a pH in a range of from about a $pH$ of 8 to about a $pH$ of 14 in the presence of a catalyst comprising a Group VIIB metal phthalocyanine and a Group VIII metal phthalocyanine at oxidation conditions. The oxidation conditions of the present invention include a temperature of from about 0° C. to about 500° C. and preferably from about 50° C. to about 400° C. and a pressure from about 1 atmosphere to about 100 atmospheres. When superatmospheric conditions are employed the excess pressure is afforded by the introduction of the oxygen-containing gas to the oxidation zone or, if so desired, the excess pressure is afforded by the pressure of the oxygen-containing gas plus any substantially inert gas such as nitrogen, helium, argon, etc., where the total pressure of the entire oxidation zone is equal to the partial pressure of oxygen-containing gas plus the partial pressure of the substantially inert gas. The oxygen-containing gas will include pure oxygen or oxygen which is present in a mixed form with a substantially inert gas, such as an oxygen-nitrogen mixture (air), oxygen-helium mixture, oxygen-argon mixture, oxygen-krypton-helium-argon mixture, oxygen-nitrogen-neon mixture, etc.

The sulfur-containing compounds of the present invention are present in either a pure form of sulfur-containing compounds or they may be intermixed in a petroleum charge stock, an aqueous charge stream or an alkali-aqueous charge stream. The sulfur-containing compounds in a petroleum charge stock may be present as natural mercaptans in a crude oil charge stock in its natural condition. Such mercaptans will vary from mercaptans possessing from about 1 carbon atom to mercaptans possessing about 19 carbon atoms. Other mercaptans which may also be present include aromatic mercaptans such as thiophenol or substituted thiophenols. It is also contemplated within the scope of this invention that the sulfur-containing compounds comprise hydrogen sulfide dissolved in an aqueous or an aqueous-alkaline solution. Specific types of mercaptans which may be converted to disulfide material by the oxidation process of this invention will include methyl mercaptans, ethyl mercaptan, propyl mercaptan, butyl mercaptan, pentyl mercaptan, hexyl mercaptan, heptyl mercaptan, octyl mercaptan, nonyl mercaptan, decyl mercaptan, undecyl mercaptan, dodecyl mercaptan, tridecyl mercaptan, tetradecyl mercaptan, pentadecyl mercaptan, hexadecyl mercaptan, heptadecyl mercaptan, octadecyl mercaptan, nonadecyl mercaptan, various mercaptobenzothiazoles, hydroxy mercaptans such as mercaptoethanol, cysteine, aromatic mercaptans such as thiophenol, methyl-substituted thiophenol isomers, ethyl-substituted thiophenol isomers, propyl-substituted thiophenol isomers, etc.

In the pure essence of this invention the catalyst system for the oxidation of the sulfur-containing compounds comprises a Group VIIB metal phthalocyanine and a Group VIII metal phthalocyanine two-component system. The catalyst system may be present in a range of from about 6 parts per Group VIIB metal phthalocyanine to about 1 part per Group VIIB metal phthalocyanine per part Group VIII metal phthalocyanine. The total catalyst system may be present in a weight percent relative to the entire reaction system of from about 0.0001 weight percent to about 10.00 weight percent. The Group VIIB metal phthalocyanine will include manganese phthalocyanine and rhenium phthalocyanine, said phthalocyanine compounds may be present in a sulfonated or a carboxylated state. For example, the Group VIIB metal phthalocyanine may comprise manganese phthalocyanine monosulfonate, manganese phthalocyanine disulfonate, manganese phthalocyanine tetrasulfonate, manganese phthalocyanine carboxylate, rhenium phthalocyanine carboxylate, rhenium phthalocyanine tetrasulfonate, rhenium phthalocyanine disulfonate, rhenium phthalocyanine monosulfonate, manganese phthalocyanine trisulfonate, rhenium phthalocyanine trisulfonate, etc. Suitable examples of Group VIII metal phthalocyanine compounds will comprise cobalt phthalocyanine, iron phthalocyanine, nickel phthalocyanine, palladium phthalocyanine, rhodium phthalocyanine, ruthenium phthalocyanine, osmium phthalocyanine, iridium phthalocyanine or platinum phthalocyanine where the Group VIII metal phthalocyanine may also be carboxylated or sulfonated. For example, the Group VIII metal phthalocyanine may comprise cobalt phthalocyanine monosulfonate, cobalt phthalocyanine disulfonate, cobalt phthalocyanine trisulfonate, cobalt phthalocyanine tetrasulfonate, ruthenium phthalocyanine monosulfonate, iron phthalocyanine disulfonate, rhodium phthalocyanine trisulfonate, osmium phthalocyanine tetrasulfonate, iridium phthalocyanine monosulfonate, nickel phthalocyanine carboxylate, palladium phthalocyanine trisulfonate, or platinum phthalocyanine tetrasulfonate, etc, The catalyst comprising the Group VIIB metal phthalocyanine and Group VIII metal phthalocyanine may also be present in the form of polymers of phthalocyanine. For example, the Group VIIB metal phthalocyanine may comprise either a polymer or monomer of manganese phthalocyanine tetrasulfonate in the same catalytic systems as either a polymer or monomer of cobalt phthalocyanine tetrasulfonate. It should again be noted that the catalyst system comprises a two-component system whereby it is necessary for the Group VIIB metal phthalocyanine and the Group VIII metal phthalocyanine to be present in conjunction with one another. However, the Group VIIB metal phthalocyanine may be present as any carboxylated or sulfonated phthalocyanine independent of the sulfonated or carboxylated Group VIII metal phthalocyanine. For example, the catalyst system of the present invention may include manganese phthalocyanine tetrasulfonate and cobalt phthalocyanine tetrasulfonate, manganese phthalocyanine disulfonate and cobalt phthalocyanine tetrasulfonate, manganese phthalocyanine tetrasulfonate and cobalt phthalocyanine disulfonate, manganese carboxylate and cobalt phthalocyanine monosulfonate, rhenium phthalocyanine tetrasulfonate and ruthenium phthalocyanine monosulfonate, manganese phthalocyanine disulfonate and rhodium phthalocyanine tetrasulfonate, rhenium phthalocyanine tetrasulfonate and cobalt phthalocyanine tetrasulfonate, manganese phthalocyanine disulfonate and palladium phthalocyanine monosulfonate, rhenium phthalocyanine monosulfonate and osmium phthalocyanine carboxylate, manganese phthalocyanine tetrasulfonate and cobalt phthalocyanine carboxylate, etc. In a preferred embodiment of this invention it is found that the catalyst system comprising the Group VIIB metal phthalocyanine and Group VIII metal phthalocyanine may be present in either an aqueous of liquid-liquid form or the catalyst system may be dispersed on a solid support such as alumina, silica, magnesia, thallia, zirconia, carbon, charcoal, γ-alumina, mordenite, faujasite, etc. The solid supports may be impregnated with reduced forms of the phthalocyanine compounds.

The process of the present invention is effected in a medium possessing a pH in a range of from about a pH of 8 to about a pH of 14. The medium which supplies the pH factor will comprise any alkaline material such as sodium hydroxide, potassium hydroxide, lithium hydroxide, rubidium hydroxide, cesium hydroxide, barium hydroxide, strontium hydroxide, calcium hydroxide, magnesium hydroxide, beryllium hydroxide, ammonia, pyridine, piperidine, picoline, lutidine, quinoline, pyrrole, indole, carbazole, acridine, or any suitable quaternary ammonium compound such as tetrabutyl ammonium hydroxide, tetraamyl ammonium hydroxide, tetrapropyl ammonium methoxide, tetraamyl ammonium methoxide, tetraethyl ammonium ethoxide, diethyl amine, triethyl amine, tetramethylenediamine, tetraethylenepentamine, phenylenediamine, however, the preferred alkaline medium will comprise either sodium hydroxide or ammonia, the sodium hydroxide being preferred when mercaptan removal is effected and the ammonium being preferred when hydrogen sulfide removal is effected. As hereinbefore set forth the pH range of the medium wil comprise a pH in the range of from about a pH of 8 to about a pH of 14. The preferred pH range will comprise a pH of from about 9 to about 13. For example, when sodium hydroxide is utilized as the treatment medium of the present invention, a pH of from about 11 to about 13 will exist within the treatment system. However, when ammonia is used a pH of from about 9 to about 13 will be present in the treatment system. It should also be noted that the treatment medium possessing a pH in the range of from about a pH of 8 to about a pH of 14 will be present in any system in which the catalyst is dispersed upon an inert support. The treatment medium is present in the solid support system by either a continual flow of the treatment medium over the solid support or the treatment medium may be intermittently contacted with the solid support.

Treatment of the charge stock containing the sulfur-containing compounds may be effected in any suitable manner and may be in a batch or continuous type process. The batch or continuous type process may both comprise either the solid bed treating or the liquid-liquid treating process. In a batch process the charge stock containing a sulfur-containing compound is introduced into the oxidation zone containing the novel catalytic system of the present invention, the treatment medium possessing a pH in the range of from about a pH of 8 to about a pH of 14 and air is introduced therein or passed therethrough. Preferably the oxidation zone is equipped with suitable stirrers or other mixing device to obtain intimate mixing. In a continuous process the treatment medium may contain the novel catalytic system of the present invention comprising a Group VIIB metal phthalocyanine and a Group VIII metal phthalocyanine, all of which is passed countercurrently or concurrently with the charge stock containing the sulfur-containing compounds in the presence of a continuous stream of air or oxygen. In a mixed type process the oxidation zone contains the treatment medium, phthalocyanine catalyst system and the charge stock and air are passed continuously therethrough and removed, generally from the upper portion of the oxidation zone. In cases of treating charge stocks containing mercaptan compounds, the resultant disulfide oxidation products may be recovered from the resultant oxidation zone effluent by any method known in the art or the disulfides may be allowed to continue through other petroleum process treating units as a harmless sulfur-containing compound. In a case in which the charge stock comprises hydrogen sulfide, the resultant sulfur product may be separated by any method known to the art and utilized in the chemical industry as a pure sulfur compound as hereinbefore set forth.

The following examples are introduced to illustrate the further novelty and utility of the present invention but not with the intention of unduly limiting the same.

EXAMPLE I

In this example 0.98 grams of thiophenol, 50 ml of isooctane 50 ml of 8% sodium hydroxide, 0.008 grams of potassium cyanide and 0.008 grams of cobalt phthalocyanine tetrasulfonate were placed in a 100 ml-round bottom flask containing a magnetic stirrer and a means of oxygen entry and uptake measurement. The oxygen uptake measurement is defined as the amount of oxygen consumed in the oxidation of the thiophenol. The desired effect is to minimize the quantity of oxygen uptake, thereby indicating the diminishment of the quantity of hydrogen peroxide (which is a partial reduction product of oxygen and is responsible for overoxidation). The potassium cyanide was added because the amount of hydrogen peroxide is maximized when the cyanide ion is present. In this manner, it is easier to compare small increments of hydrogen peroxide formation. The flask was maintained at a temperature of 20° C. and a pressure of 1 atmosphere as afforded by the introduction of oxygen to the oxidation flask for a period of time comprising 19 minutes, which was the approximate 100% oxidation time. The oxygen uptake was measured at the end of this period of time, said oxygen uptake being 80.5 ml/gram of thiophenol at standard pressure and temperature.

EXAMPLE II

In this example 0.73 grams of thiophenol, 50 ml of isooctane, 50 ml of 8% sodiumhhydroxide, 0.008 grams of potassium cyanide and 0.034 grams of cobalt phthalocyanine tetrasulfonate were placed in a 100 ml-round bottom flask containing a magnetic stirrer and a means of oxygen entry and uptake measurement. The flask was maintained at a temperature of 20° C. and a pressure of 1 atmosphere as afforded by the introduction of oxygen to the oxidation flask for a period of time comprising 13 minutes, which was the approximate 100% oxidation time. The oxygen uptake was measured at the end of this period of time, said oxygen uptake being 71.8 ml/grams of thiophenol at standard pressure and temperature.

EXAMPLE III

In this example 1.00 grams of thiophenol, 50 ml of isooctane, 50 ml of 8% sodium hydroxide, 0.008 grams of potassium cyanide and a catalyst system comprising 0.008 grams of cobalt phthalocyanine tetrasulfonate and 0.026 grams of manganese phthalocyanine tetrasulfonate (a 3:1 ratio of manganese species to cobalt species) was added to a 100 ml-round bottom flast containing a magnetic stirrer and a means of oxygen entry and uptake measurement. The oxygen uptake is defined as set forth in Example I. The oxidation flask was maintained at the conditions of pressure and temperature of Examples I and II for a period of time comprising 15 minutes, which was the approximate 100% oxidation time. The oxygen uptake was measured at the end of this period of time, said oxygen uptake being 42.2 ml/gram of thiophenol at standard pressure and temperature.

The unexpected results of the present invention may be cogently seen in a comparison of Example III with Examples I and II. In Example III a catalyst system comprising a Group VIIB metal phthalocyanine and a Group VIII metal phthalocyanine was utilized in comparison to the Group VIII metal phthalocyanine of Examples I and II. The result of the different catalyst system in Example III was the oxygen uptake of only 42.2 ml/gram of thiophenol at STP in comparison with the oxygen uptake of 80.5 ml/gram of thiophenol at STP of Example I and the 71.8 ml/gram of thiophenol at STP of Example II. The difference in the respective numbers shows that less overoxidation occurred in Example III, since substantially less hydrogen peroxide was present than in the Examples I and II, which utilized a catalyst known in the art.

EXAMPLE IV

In this example 1.11 grams of thiophenol, 50 ml of isooctane, 50 ml of 8% sodium hydroxide, 0.008 grams of potassium cyanide and a catalyst system comprising 0.008 grams of cobalt phthalocyanine tetrasulfonate and 0.008 grams of manganese phthalocyanine tetrasulfonate (a 1:1 ratio of the manganese species to the cobalt species) was added to a 100 ml-round bottom flask containing a magnetic stirrer and a means of oxygen entry and uptake measurement. The oxidation flask was maintained at the conditions of pressure and temperature of Examples I, II and III for a period of time comprising 17 minutes, which was the approximate 100% oxidation time. The oxygen uptake was measured at the end of this period of time, said oxygen uptake being 50.4 ml/gram of thiophenol at standard pressure and temperature.

It should be noted that in a comparison of Example IV to Example III that the amount of hydrogen peroxide was increased with the change from the 3:1 metal species ratio to the 1:1 metal species ratio. However, in the comparison of Example IV to Examples I and II it can be seen that the amount of oxygen uptake, or hydrogen peroxide formation, the relative value was still decreased using the 1:1 metal species ratio in contrast to the known catalytic metals of Examples I and II which showed an oxygen uptake of 80.5 ml/gram of thiophenol at STP for Example I and 71.8 ml/gram of thiophenol at STP for Example II.

EXAMPLE V

In this example 1.50 grams of thiophenol, 50 ml of isooctane, 50 ml of 8% sodium hydroxide, 0.008 grams of potassium cyanide and a catalyst system comprising 0.014 grams of cobalt phthalocyanine tetrasulfonate and 0.007 grams of manganese phthalocyanine disulfonate (a 2:1 ratio of cobalt species to the manganese species) was added to a 100 ml-round bottom flask containing a magnetic stirrer and a means of oxygen entry and uptake measurement. It should be noted in this experiment that a disulfonate of one metal of the two-component system is utilized in conjunction with a tetrasulfonated metal of the two-component system in contrast to the previous examples which have all compared the metal tetrasulfonates in combination with each other. The oxidation flask was maintained at a temperature of 20° C. and a pressure of 1 atmosphere as afforded by the introduction of oxygen to the oxidation flask for a period of time comprising 23 minutes, which was the approximate 100% oxidation time. The oxygen uptake was measured at the end of this period of time, said oxygen uptake being 53.5 ml/gram of thiophenol at STP.

It should be noted that a comparison of Example III with Examples I and II show a decrease in the hydrogen peroxide formed (lower oxygen uptake values) utilizing the Group VIIB metal disulfonate in conjunction with the Group VIII metal tetrasulfonate (cobalt phthalocyanine tetrasulfonate), which was previously known in the art.

EXAMPLE VI

In this example 1.54 grams of thiophenol, 20 ml of isooctane, 50 ml of 8% sodium hydroxide, and 0.05 grams of cobalt phthalocyanine tetrasulfonate dispersed on 50.00 grams of Nuchar WA (a charcoal compound produced under the trademark Nuchar WA) was added to a 100 ml-round bottom flask containing a magnetic stirrer and a means of oxygen entry and uptake measurement. The oxidation flask was maintained at conditions of 20° C. and a pressure of 1 atmosphere for a period of time comprising 30 minutes, which was the approximate 100% oxidation time. The oxygen uptake at the end of this period of time was measured, said oxygen uptake being 62.7 ml/gram of thiophenol at STP.

It should be noted that this example is included within the specification to show the increased advantage of treating a sulfur-containing compound with the bimetallic catalyst system of Example VII, this example, Example VI, utilizing only the monometallic catalyst system which was previously known in the art.

EXAMPLE VII

In this example 1.53 grams of thiophenol, 20 ml of isooctane, 50 ml of 8% sodium hydroxide, 0.008 grams of potassium cyanide and a catalyst system comprising 0.90 grams of manganese phthalocyanine tetrasulfonate and 0.15 grams of cobalt phthalocyanine tetrasulfonate dispersed on 45.00 grams of charcoal was added to a 100 ml-round bottom flask containing a magnetic stirrer and a means of oxygen entry and uptake measurement. The oxidation flask was maintained at the conditions of temperature and pressure of experiment VI for a period of time comprising 42.5 minutes which was the approximate 100% oxidation time. The oxygen uptake was measured at the end of this period of time, said oxygen uptake being 48.0 ml/gram of thiophenol at STP.

It should be noted that a comparison of Example VI with Example VII will show a decrease in the amount of oxygen uptake from 62.7 ml/gram of thiophenol at STP of Example VI to the 48.0 ml/gram of thiophenol at STP oxygen uptake of Example VII. The decrease in the oxygen uptake as hereinbefore set forth indicates the lower amount of hydrogen peroxide present in Example VII, thereby alleviating problems of caustic use and color generation.

EXAMPLE VIII

In this example 1.56 grams of methyl mercaptan, 0.010 grams of potassium cyanide in a vaporous phase and a catalyst system comprising 0.50 grams of rhenium phthalocyanine disulfonate and 0.50 grams of ruthenium phthalocyanine tetrasulfonate dispersed on 25.6 grams of alumina is added to a 100 ml-round bottom flask containing a medium comprising tetrabutyl ammonium hydroxide, a magnetic stirrer and a means of air entry and air uptake measurement. The oxidation flask is maintained at oxidation conditions of 150° C. and a pressure of 5 atmospheres as afforded by the introduction of air to the reaction system for a period of time comprising 15 minutes, which is the approximate 100% oxidation time of the methyl mercaptan. The air uptake is measured at the end of this period of time, said air uptake being equal to an amount less than that of a controlled standardized example utilizing only the rhenium phthalocyanine disulfonate.

EXAMPLE IX

In this example 0.52 grams of sodium sulfide, 50 ml of 4% sodium hydroxide and 0.10 grams of cobalt phthalocyanine tetrasulfonate was added to a 100 ml- round bottom flask containing a magnetic stirrer and a means of oxygen entry and uptake measurement. The oxidation flask was maintained at oxidation conditions of 20° C. and a pressure of 1 atmosphere as afforded by the introduction of oxygen to the reaction system for a period of time comprising approximately 130 minutes, which was the approximate 100% oxidation time. The oxygen uptake was measured at the end of this time, said oxygen uptake being 183.0 ml/gram sulfide at STP. It should be noted that the purpose of this example was to compare the monometallic catalyst system known to the art of this example with the hereinafter set forth Example X which discloses the unexpected utilizing the two-component catalyst system.

EXAMPLE X

In this example 0.53 grams of sodium sulfide, which was partially converted to hydrogen sulfide before oxidation, 50 ml of 4% sodium hydroxide, 0.10 grams of cobalt phthalocyanine tetrasulfonate and 0.30 grams of manganese phthalocyanine tetrasulfonate (a 3:1 ratio of manganese species to cobalt species) was added to a 100 ml-round bottom flask containing a magnetic stirrer and a means of oxygen entry and uptake measurement. The oxidation flask was maintained at the same physical conditions of Example IX for a period of time comprising 125 minutes, which was the approximate 100% oxidation time. The oxygen uptake was measured at the end of this period of time, said oxygen uptake being 157.0 ml/gram sulfide at STP.

It can be seen as a comparison of Examples IX and X that the catalyst system of the present invention provided unexpected results in the fact that less oxygen uptake was recorded utilizing the two-component catalyst systems. However, it should be noted that in the case of the hydrogen sulfide the decreased amount of oxygen uptake does not mean less formation of hydrogen peroxide as in the case of the oxidation of the thiophenol or mercaptan compound. The smaller the oxygen uptake of the example, the smaller the quantity of thiosulfate production from the oxidation of the sodium sulfide and the more sulfur.

EXAMPLE XI

In this example a catalyst comprising 1.1 grams of manganese phthalocyanine tetrasulfonate and 0.15 grams of cobalt phthalocyanine tetrasulfonate on 45 grams of Darco 12 × 20 (a tradename for an activated charcoal compound sold under the name Darco 12 × 20) was prepared and utilized for the oxidation of a charge stock comprising a liquid feed of 5.63 grams of sulfur as ammonium sulfide per hour (this sulfur being derived from hydrogen sulfide), and 0.73 grams of ammonium thiosulfate per hour for a total of 6.36 grams of sulfur per hour. The temperature was maintained at 52° C. and the pressure was maintained at 5 atmospheres, circulation of charge was at a liquid hourly space velocity (LHSV) of 1.0 with a 90% stoichiometric quantity of air. The resultant oxidation product was recovered, analyzed and found to contain only 0.72 grams of sulfur as ammonium thiosulfate, said result being unexpected in the fact that an experiment utilizing a catalyst known to the art would have resulted in the conversion of 7–14% of the ammonium sulfide to ammonium thiosulfate. The oxidation product also indicates a 69.6 percent conversion of ammonium sulfide to ammonium polysulfide. It can be seen from the treatment of the two-component catalytic system of the present invention that the amount of thiosulfate compound was drastically reduced in the presence of the novel catalyst system of the present invention.

I claim:

1. A process for the oxidation of a sulfur-containing compound which comprises treating said sulfur-containing compound at oxidation conditions with an oxygen-containing gas in a medium possessing a pH in a range of from about a pH of 8 to about a pH of 14 in the presence of a catalyst system comprising a Group VIIB metal phthalocyanine and a Group VIII metal phthalocyanine in a ratio of from about 1 to about 6 mols of the Group VIIB metal phthalocyanine per mol of the Group VIII metal phthalocyanine to decrease the uptake of oxygen, and recovering the resultant oxidized sulfur-containing compound.

2. The process of claim 1 further characterized in that said catalyst system comprises about 3 parts of the Group VIIB metal phthalocyanine and about 1 part of the Group VIII metal phthalocyanine.

3. The process of claim 1 further characterized in that the oxidation conditions include a temperature of from about 0° C. to about 500° C. and a pressure of from about 1 atmosphere to about 100 atmospheres.

4. The process of claim 1 further characterized in that the sulfur-containing compound is a mercaptan.

5. The process of claim 4 further characterized in that the mercaptan is methyl mercaptan.

6. The process of claim 4 further characterized in that the mercaptan is propyl mercaptan.

7. The process of claim 4 further characterized in that the mercaptan is thiophenol.

8. The process of claim 1 further characterized in that the sulfur-containing compound is hydrogen sulfide.

9. The process of claim 1 further characterized in that the oxygen-containing gas is oxygen.

10. The process of claim 1 further characterized in that the oxygen-containing gas is air.

11. The process of claim 1 further characterized in that the Group VIIB metal phthalocyanine is manganese phthalocyanine and the Group VIII metal phthalocyanine is cobalt phthalocyanine.

12. The process of claim 1 further characterized in that the Group VIIB metal phthalocyanine is rhenium phthalocyanine and the Group VIII metal phthalocyanine is ruthenium phthalocyanine.

13. The process of claim 1 further characterized in that the Group VIIB metal phthalocyanine is manganese phthalocyanine and the Group VIII metal phthalocyanine is iridium phthalocyanine.

14. The process of claim 1 further characterized in that the Group VIIB metal phthalocyanine is rhenium phthalocyanine and the Group VIII metal phthalocyanine is cobalt phthalocyanine.

15. The process of claim 1 further characterized in that the Group VIIB metal phthalocyanine is manganese phthalocyanine and the Group VIII metal phthalocyanine is nickel phthalocyanine.

16. The process of claim 1 further characterized in that the catalyst system is dispersed on a solid support.

17. The process of claim 16 further characterized in that the solid support is carbon.

18. The process of claim 16 further characterized in that the solid support is γ-alumina.

19. The process of claim 1 further characterized in that the medium comprises sodium hydroxide.

20. The process of claim 1 further characterized in that the medium comprises ammonia.

21. The process of claim 1 further characterized in that the medium comprises a quaternary ammonium compound.

22. The process of claim 21 further characterized in that the quaternary ammonium compound is tetrabutyl ammonium hydroxide.

23. The process of claim 21 further characterized in that the quaternary ammonium compound is tetraamyl ammonium methoxide.

* * * * *